Figure 1:
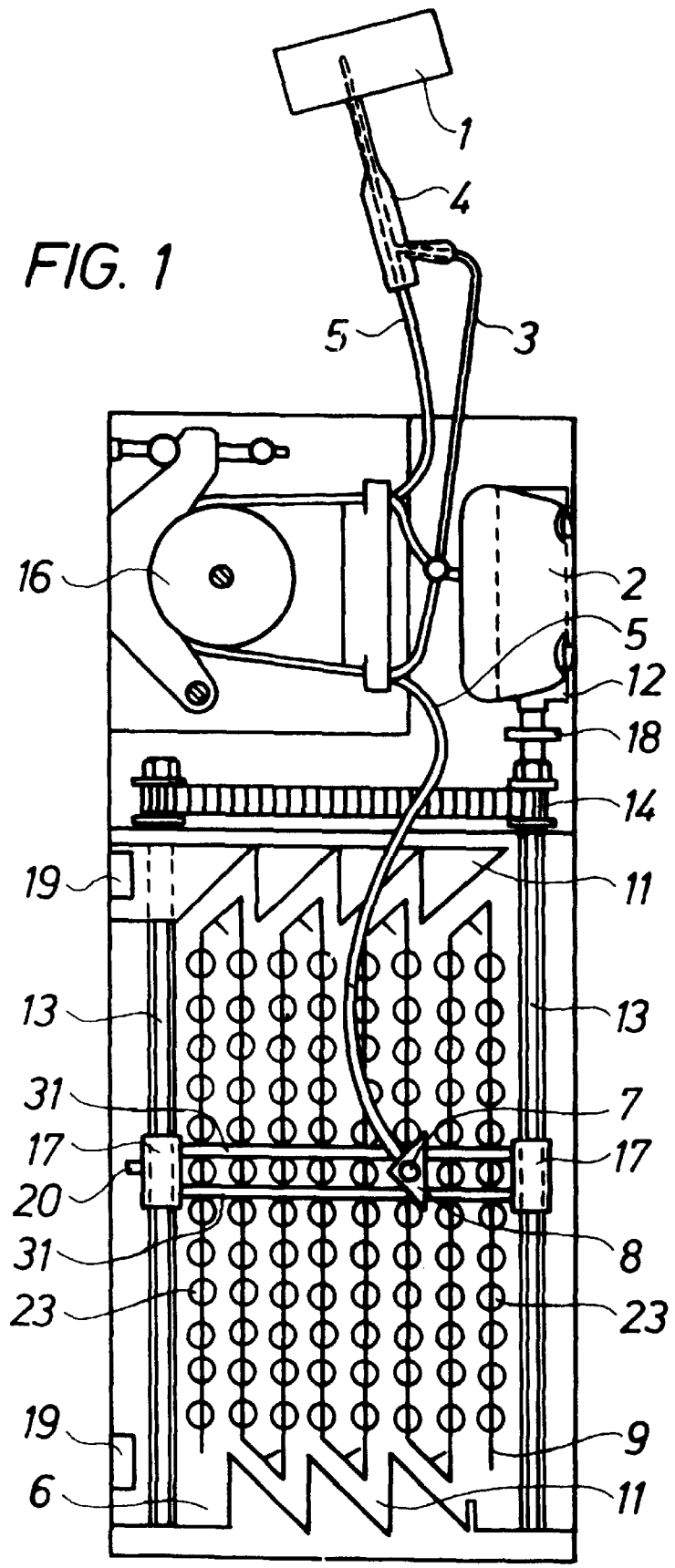

United States Patent
Nylen

[11] Patent Number: 5,942,441
[45] Date of Patent: Aug. 24, 1999

[54] METHOD AND DEVICE FOR COLLECTION OF LIQUID SAMPLES

[75] Inventor: Ulf Nylen, Lund, Sweden

[73] Assignee: Stemu AB, Lund, Sweden

[21] Appl. No.: 08/666,404

[22] PCT Filed: Nov. 14, 1994

[86] PCT No.: PCT/SE94/01063

§ 371 Date: Aug. 12, 1996

§ 102(e) Date: Aug. 12, 1996

[87] PCT Pub. No.: WO95/16632

PCT Pub. Date: Jun. 22, 1995

[30] Foreign Application Priority Data

Dec. 17, 1993 [SE] Sweden .................................. 9304193

[51] Int. Cl.$^6$ .............................. G01N 1/18; B67D 5/00
[52] U.S. Cl. ........................... 436/179; 436/54; 436/174; 436/180; 422/63; 422/65; 422/100; 422/102; 422/104; 141/130; 73/864.01
[58] Field of Search ................................. 436/43, 54, 174, 436/179, 180, 183; 422/63, 65, 99, 100, 104, 102; 141/130, 329; 73/864.01, 864.91

[56] References Cited

U.S. PATENT DOCUMENTS

| | | | |
|---|---|---|---|
| 3,450,173 | 6/1969 | Maizel, Jr. | 141/130 |
| 3,623,515 | 11/1971 | Gilson | 141/130 |
| 3,999,949 | 12/1976 | Andersson et al. | 23/259 |
| 4,362,698 | 12/1982 | Boosalis et al. | 422/102 |

FOREIGN PATENT DOCUMENTS

WO 87/07911  12/1987  WIPO .

*Primary Examiner*—Long V. Le
*Attorney, Agent, or Firm*—Merchant Gould Smith Edell Welter & Schmidt

[57] ABSTRACT

Device for collection of liquid samples has a pump (16) for pumping sampling liquid (24), a tube (7) for delivering the sampling liquid, sample container (23) for collection of the sampling liquid, and a transport device for moving the tube in succession from one sample container to the next sample container in at least one row of sample containers. An elastic cloth (22) is sealingly applied over the openings of the sample containers, and a slit (21), in which the tube (7) runs, is arranged in the cloth. The transport device is arranged to stop the tube when it is in a position over the sample container.

14 Claims, 3 Drawing Sheets

METHOD AND DEVICE FOR COLLECTION OF LIQUID SAMPLES

The invention refers to a method for collection of liquid samples as well as a device for carrying out the method according to the invention. More specifically, the invention refers to a method in which a sampling liquid is delivered by means of a pump to a sample container via a tube which is moved by a transport device in succession from one sample container to the next sample container in several rows of sample containers, the tube after the last sample container in a row being moved to the nearest sample container in the next row.

When medicinal samples are taken—as well as in other instances—a person has to go to the patient or to a place for sampling in order to obtain the necessary sample by means of a canula or some other sampling instrument. This procedure has to be repeated each time a sample is taken. If kinetic changes are to be followed the sampling has to take place with some regularity so that concentration changes with time can be determined with any relevance in subsequent analyses.

The most usual way to regularly take medicinal samples is that somebody inserts a canula into the patient and collects a sample of intervals of for with half an hour. The samples are then transported to another place for analysis, e.g. a laboratory. However, when the results from the analysis are not of acute significance the analysis of the samples can wait until all the samples have been taken.

Apparatuses for regular sampling of blood are described. These apparatuses, built around conventional fraction collectors, are big and can not easily be carried. The patient must thus remain in the vicinity of the permanently stationed apparatus. Systems are also described in which the analysis of the sample takes place continuously. In these cases the analysis is usually based on the determination of glucose. Such a system is described in U.S. Pat. No. 4,123,353.

In more expensive systems for blood sampling the results from the analysis are utilized directly, e.g for regulating the dosage of insulin. On the other hand, if the results from the analysis are not to be used until a test series is completed the same information can be obtained if the laboratory analyses all the samples afterwards. Furthermore, if separate samples are collected at a certain sampling several different types of analyses can advantageously be performed on the same sample.

In order to further facilitate a flexible use the apparatus should be designed to be portable. However, a simple portable system for continuous blood sampling or other kinds of sampling does not exist on the market. An essential prerequisite for a portable equipment is that the liquid samples are not spilled. Furthermore, it is desirable if the samples, when necessary, can be handled aseptically.

The purpose of the present invention is to facilitate and simplify the method of regular or continuous sampling above all during blood sampling by using a portable device which gives a low manufacturing cost. The device for collection of liquid samples according to the invention in includes a special fraction collector which is so constructed that the samples are not spoiled even if the device is turned sideways or upside down.

In order to achieve this purpose the invention has obtained the characterizing features of claim 1 and 9.

Figure 2A:
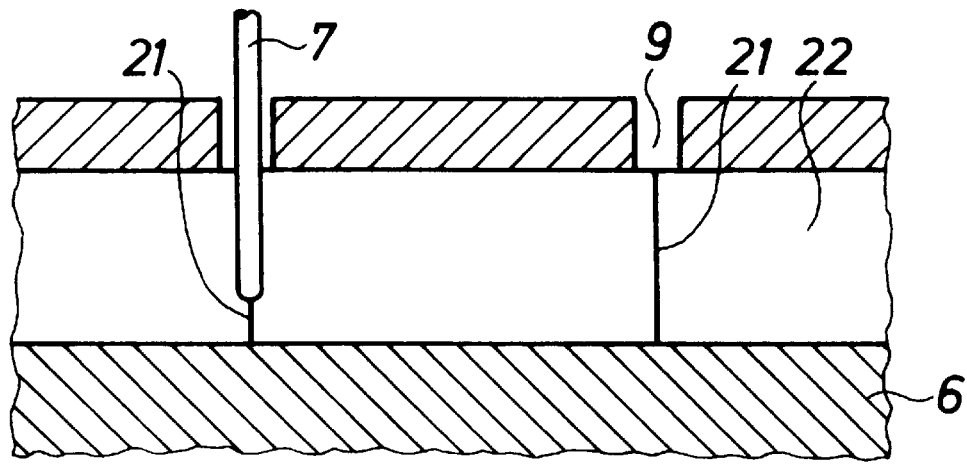
Figure 2B:
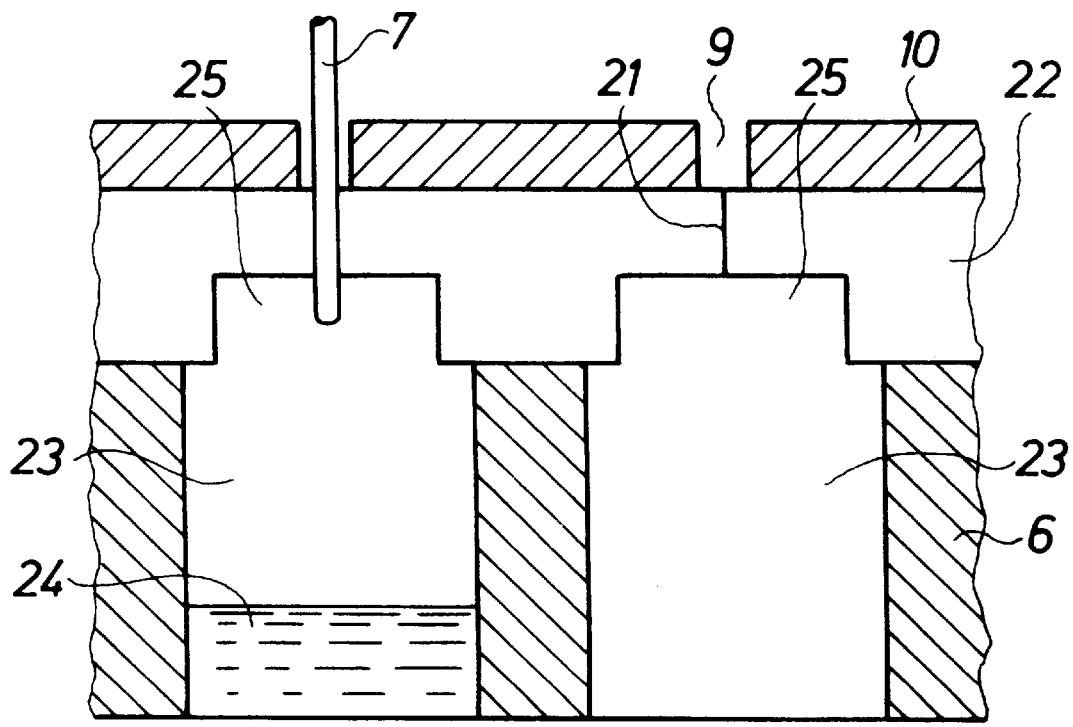
Figure 3:
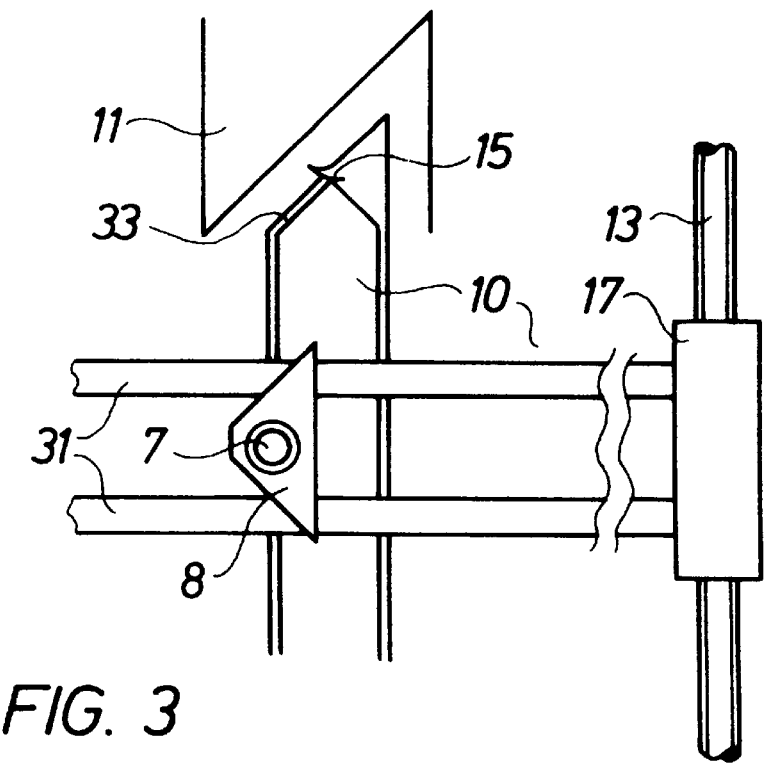
Figure 4:
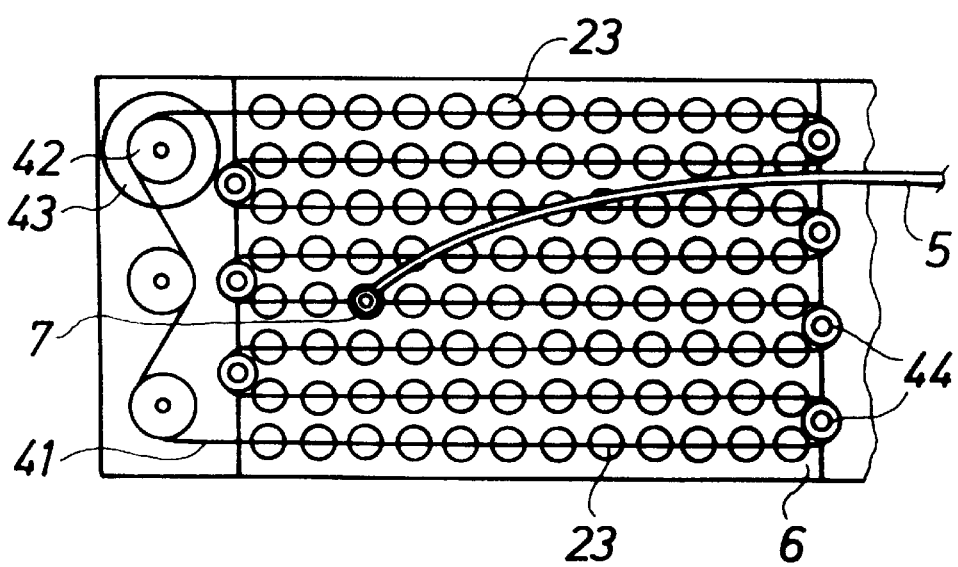

In order to explain the invention in more detail two embodiments thereof will be described below reference being made to the accompanying drawings in which FIG. 1 is an overall view of a device according to the invention, FIG. 2A is a detail view of the device in cross section, FIG. 2B corresponds to FIG. 2A but shows another cross section which illustrates another point of the course of sampling, FIG. 3 is a detail view of the device according to FIG. 1, and FIG. 4 shows another embodiment of a device according to the invention.

In the overall view of FIG. 1 a sample is sucked out at a sampling point 1. The sample can be blood or some other liquid or suspension which is to be analyzed. At the same time as the sample is sucked out it is usually diluted and mixed with a diluent. This preferably takes place in the tip of a double-lumen catheter 4. The diluent is pumped by a pump 16 from a container 2 with diluent to the catheter 4 via a tubing 3. The same pump 16 is used to pump the mixed sampling liquid 24 via a tubing 5 to a tube 7 which ends over a sample container 23 in a fraction collector in which the sample containers are arranged in parallel rows. In a preferred embodiment of the invention the fraction collector is designed with the sample containers arranged in parallel rows but fraction collectors can also be used with the sample containers arranged in a spiral shaped pathway or the like.

The diluent can contain one or several substances which prevent the contents from being coagulated or destroyed in other ways. These substances can also be added to the sample containers in advance in a soluble or solid form. The surface in the tubing 5 can also be covered with for example an inhibitor which can either be immobilized or be slowly released into the sampling liquid.

After the sample container 23 has been filled with sampling liquid the tube is moved to the next sample container and so on. When the last sample container in one row has been filled with sampling liquid the tube is moved to the nearest sample container in the next row in one of several rows of sample containers. The sample containers preferably consist of wells in a microtiter plate and the tube 7 is a canula, but other embodiments can also be suitable for specific applications.

In order to prevent the samples from leaking out from the filled sample containers these can be covered by a septum which is penetrated by the canula in every container. This procedure is preferred if it is required that the samples must be handled sterilely. However, an shown in FIG. 2A, it is preferred that the containers are covered with an elastic cloth 22 having a slit 21 in which the tube 7 can run. Recesses 25 are arranged in the cloth facing the sample containers 23, the diameter of which preferably being a little smaller than the diameter of the sample containers. The recesses are preferably centered exactly over the openings of the containers. When the tube in the cloth 22 is brought to follow the slit 21 between two sample containers 23 the tube does not completely penetrate the cloth. However, in the recesses 25 over each sample container, FIG. 2B, the tube reaches so far down within the slit that the tip of the tube runs free from the elastic cloth. By this design of the elastic cloth it is avoided that sampling liquid penetrates into the slit when the liquid leaves the tube and that liquid is transferred between the sample containers. If a sterile procedure is not absolutely necessary this handling of the sample is sufficient.

In this embodiment, a guiding plate 10 of some stiff material is arranged over the elastic cloth 22 for the purpose of guiding the tube 7 in the slit 21, above all when turned after the last sample container in one row towards the nearest sample container in the next row. Slots 9 are punched in the guiding plate 10 and are located immediately over the corresponding slits in the cloth. In other applications a device corresponding to the guiding plate is arranged at the end of each row of sample containers.

When turned between rows of sample containers the tube is forced over to the next row by means of a guiding device. In a preferred embodiment of the invention, FIG. 3, the tube 7 is attached in the middle of a triangular guiding sledge 8 which preferably is arranged to slide along two smooth bars 31 arranged perpendicular to the rows of sample containers. The sledge can be arranged to elide in other ways, e.g. in a groove on a bar.

The bars are in both ends attached to screw pieces 17 which are forced forwards or backwards by means of rotating screw bars 13, a toothed belt 14 and a motor 12 which operates the screw bars 13 via the toothed belt 14. The whole part in which the sledge runs is moved forwards when the tube is moved from one sample container to the next sample container. The position of the sledge is controlled by a revolution counter 18 as well as an end point and starting point reader 19. The reader registers when a portion of the screw piece is immediately opposite the end point or the starting point. In a preferred embodiment of the invention the reader 19 is used only in the beginning of the sampling, and the remaining control of the position of the tube 7 is handled by a revolution counter 18. The revolution counter registers the number of revolutions of the screw bars 13. The rotation of the screw bars corresponds to a displacement of the guiding sledge 8 along the row of sample containers. By measuring the rotation of the screw bars it is possible to determine the position of the tube 7 so that it can be guided to be moved between two sample containers in a row. The signals from the revolution counter 18 are also used for changing the direction of the motor 12 at the end of each row of sample containers so that the tube 7 follows a zigzag formed pathway along all the sample containers.

When a row of sample containers, usually 12, have been filled the sledge together with its tube is forced over to the next row of sample containers either by means of the slots 9 in the guiding plate or by means of an inclined deflection bar 11 which facilitates the passage of the tube 7 to the next row of sample containers. The passage takes place in such a way that the sledge continues in the same direction after the last sample container in one row has been filled with sampling liquid. Then at 33 the downward projecting tube 7, and thus the sledge 8, are forced aside by the deflecting slot 9 in the guiding plate 10. However, an inclined deflection bar 11 preferably assists in the passage by forcing aside the triangular sledge 8 in this case. The slot 9 in the underlying guiding plate 10 is then at 33 arranged to follow the pathway of the sledge 8 and thus the tube 7, the pathway coincides with the inclined motion the sledge is forced to make. At the same time the tube passes a flap 15 in the rigid plate 10, which is located approximatively where the elastic cloth ends. After this point the slot 9 in the guiding plate passes into an open area.

When the motor 12 operating the part including the sledge changes rotational direction the tube will be forced into the next slot 9 in the guiding plate 10 by the inclined design of the plate above the flap 15. Then the tube is forced into the corresponding slot 21 in the cloth 22. The flap mentioned above thus prevents the tube from returning to the slot from which it came.

FIG. 4 shows a second embodiment for guiding the tube from one sample container to the next sample container, an alternative guiding device for transferring the tube 7 from one slit in a row of sample containers to the next slit in the next row of sample containers being shown at the same time. In this case the tube 7 above the elastic cloth is attached to an endless band 41 The band runs around turning wheels 44 arranged at the ends of the rows of sample containers between these In order to ensure a proper position for the tube when it discharges liquid to the sample containers the band is preferably easily deflectable laterally but is non-extensible. The band is pulled from the first sample container in one corner of the sample plate 6 to the last sample container in the diagonal corner by a motor 43 with driving wheels 42. At the passage between two rows of sample containers the band 41 pulls the tube 7 around the turning wheel 44. In this case the slit in the elastic cloth as well as the slot in the rigid plate runs around the turning wheel 44 to the next row. Since the band 44 provides sufficient steadiness to the tube 7 the rigid guiding plate can be omitted in this embodiment of the invention. Nor is a flap required for preventing the tube from returning to the same slit since the tube is advanced in the same direction. The guiding plate can also be omitted when another type of pathway is chosen.

In practice, at continuous operation the design of the device according to the invention implies a time difference of about 3 minutes from the time of sampling at the sampling point 1 until the sample is delivered into a sample container 23. The sampling pump is working as the sample containers are filled, which takes 3 minutes, and the volume from the sampling point 1 to the tube 7 thus corresponds to the volume of one sample container. The pump is stopped when the tube 7 is moved between the containers. If sampling has to take place during a considerable period of time the system can be designed electronically so that the sampling takes place more slowly. This means that the pump 16 works intermittently. If, for example, a sample for one container is to be sampled during 10 minutes in stead of 3 minutes the pump works for 6 seconds and is idle for 14 seconds, and this sequence is repeated those 30 times which are required for filling one container. The same procedure is repeated for the remaining containers. The advantage of this procedure is that blood corpuscles etc. do not remain stationary in the tubings for a long continuous period of time and at the same time the length of tubing from the sampling point 1 to the tube 7 will not become critical.

I claim:

1. Method for collection of liquid samples, wherein the sampling liquid is delivered by means of a pump to a sample container via a tube which is moved by a transport device in succession from one sample container to the next sample container in at least one row of sample containers, and the sampling liquid is delivered to the sample containers one at a time with the tube positioned over a sample container comprising the step of:

providing an elastic cloth which is sealingly applied over openings of the sample containers and extending over the row of sample containers; and bringing the tube to follow a pathway in the form of a slit arranged in the cloth, the slit extending over the openings of the containers along the row of sample containers.

2. Method as claimed in claim 1, wherein the tube is brought to stop when the mouth of the tube is in a recess in the lower surface of the elastic cloth over a sample container.

3. Method as claimed in claim 1, wherein the tube is mounted to a carrier which is moved along a guide.

4. Method as claimed in claim 1, wherein the tube after the last sample container in a row is guided from this row of sample containers over to the next row of sample containers by means of a guiding device when there are several rows of sample containers.

5. Method as claimed in claim 4, wherein the tube when passing from one row to the next row is guided by a guiding plate arranged over the slit.

6. Method as claimed in claim 4, wherein the tube when passing from one row of sample containers to the next row of sample containers is prevented by a flap from returning to the previous row of sample containers.

7. Method as claimed in claim 1, wherein the tube is carried and imparted movement by an endless band which runs along a plurality of rows of sample containers and over turning wheels is passed from one row to the next.

8. Device for collection of liquid samples comprising a pump fluidly connected to a tube for delivering the sampling liquid, sample containers for collection of the sampling liquid arranged in at least one row, and a transport device for moving the tube in succession from one sample container to the next sample container along the row of sample containers, an elastic cloth sealingly applying over openings of the sample containers, and a slit formed in the elastic cloth extending over the openings of the containers along the row of sample containers wherein the tube is movable.

9. Device as claimed in claimed 8, wherein the tube is mounted to a carrier which is movably guided on a guide arranged along the slit.

10. Device as claimed in claim 8, a plurality of rows of sample containers are arranged, and a guiding device is arranged after the last sample container in a row for guiding the tube from this row of sample containers over to the next row of sample containers.

11. Device as claimed in claim 10, wherein the tube is attached to and carried by an endless band which is advanced along a plurality of rows of sample containers and is guided over turning wheels from one row of sample containers to the next row of sample containers.

12. Device as claimed in claim 8, wherein a guiding plate is arranged over the slit, in which a slot is arranged in order to force the tube to follow a pathway of the slit.

13. Device as claimed in claim 9, wherein the guide is perpendicular to the rows of sample containers, and the guide in its ends is attached to means for transportation of the guide along the rows of sample containers.

14. Device as claimed in claim 8, wherein a recess is arranged over each sample container in the lower surface of the elastic cloth.

\* \* \* \* \*